(12) United States Patent
Rokde

(10) Patent No.: US 9,918,863 B2
(45) Date of Patent: Mar. 20, 2018

(54) STEERABLE GASTRIC CALIBRATION TUBE

(71) Applicant: Covidien LP, Mansfield, MA (US)

(72) Inventor: Rajat R. Rokde, Chandanagar Hyderabad (IN)

(73) Assignee: Covidien LP, Mansfield, MA (US)

( * ) Notice: Subject to any disclaimer, the term of this patent is extended or adjusted under 35 U.S.C. 154(b) by 593 days.

(21) Appl. No.: 14/078,731

(22) Filed: Nov. 13, 2013

(65) Prior Publication Data

US 2015/0133857 A1 May 14, 2015

(51) Int. Cl.
*A61F 5/00* (2006.01)
*A61M 25/01* (2006.01)
*A61B 17/00* (2006.01)

(52) U.S. Cl.
CPC ....... *A61F 5/0089* (2013.01); *A61M 25/0147* (2013.01); *A61B 2017/003* (2013.01); *A61B 2017/00305* (2013.01); *A61B 2017/00323* (2013.01); *A61B 2217/007* (2013.01)

(58) Field of Classification Search
CPC ........... A61B 2017/00818; A61B 2017/00827; A61B 2017/003; A61M 25/0138; A61M 25/0147
See application file for complete search history.

(56) References Cited

U.S. PATENT DOCUMENTS

| 3,227,154 | A | | 1/1966 | Cook | |
|---|---|---|---|---|---|
| 3,557,780 | A | * | 1/1971 | Sato | A61B 1/0055 356/241.4 |
| 4,328,805 | A | | 5/1982 | Akopov et al. | |
| 5,203,380 | A | * | 4/1993 | Chikama | A61B 1/0055 138/118 |
| 5,231,989 | A | * | 8/1993 | Middleman | A61B 1/00165 600/434 |
| 5,297,536 | A | | 3/1994 | Wilk | |
| 5,382,231 | A | | 1/1995 | Shlain | |
| 5,401,241 | A | | 3/1995 | Delany | |
| 5,458,131 | A | | 10/1995 | Wilk | |
| 5,462,528 | A | | 10/1995 | Roewer | |
| 5,465,709 | A | | 11/1995 | Dickie et al. | |

(Continued)

FOREIGN PATENT DOCUMENTS

CN 201365906 Y 12/2009
CN 102626536 A 8/2012

(Continued)

OTHER PUBLICATIONS

Extended European Search Report dated Oct. 1, 2015, corresponding to European Application No. 15167342.3; 7 pages.

(Continued)

*Primary Examiner* — Alexander Orkin

(57) ABSTRACT

A gastric calibration tube includes an elongate member and an adjusting member. The elongate member has a length and includes a first segment and a second segment that extend along the length. The second segment includes a first side and a second side. The first and second sides are selectively movable in opposite lengthwise directions. The adjusting member is secured to one of the sides of the second segment and movable with the second segment relative to the first segment to steer the elongate member.

18 Claims, 3 Drawing Sheets

(56) References Cited

U.S. PATENT DOCUMENTS

| | | | |
|---|---|---|---|
| 5,718,666 A | 2/1998 | Alarcon | |
| 6,013,024 A * | 1/2000 | Mitsuda | A61B 1/00039 600/146 |
| 6,558,400 B2 | 5/2003 | Deem et al. | |
| 7,153,131 B2 | 12/2006 | Crohn | |
| 7,713,281 B2 | 5/2010 | Leeflang et al. | |
| 7,744,613 B2 | 6/2010 | Ewers et al. | |
| 7,883,524 B2 | 2/2011 | Chen | |
| 7,918,869 B2 | 4/2011 | Saadat et al. | |
| 8,016,851 B2 | 9/2011 | Dillon et al. | |
| 8,092,378 B2 | 1/2012 | Roth et al. | |
| 8,147,502 B2 | 4/2012 | Albrecht et al. | |
| 8,192,448 B2 | 6/2012 | Bessler et al. | |
| 8,216,271 B2 | 7/2012 | Kassab et al. | |
| 8,454,503 B2 | 6/2013 | Roth et al. | |
| 8,663,149 B2 | 3/2014 | Gagner et al. | |
| 2002/0161281 A1* | 10/2002 | Jaffe | A61B 1/0008 600/114 |
| 2004/0006351 A1 | 1/2004 | Gannoe et al. | |
| 2004/0092974 A1 | 5/2004 | Gannoe et al. | |
| 2004/0138525 A1* | 7/2004 | Saadat | A61B 1/0055 600/104 |
| 2004/0193146 A1* | 9/2004 | Lee | A61B 17/062 606/1 |
| 2004/0249367 A1* | 12/2004 | Saadat | A61B 1/0055 606/1 |
| 2005/0096694 A1* | 5/2005 | Lee | A61B 17/00234 606/205 |
| 2005/0119674 A1 | 6/2005 | Gingras | |
| 2005/0159769 A1 | 7/2005 | Alverdy | |
| 2005/0203489 A1 | 9/2005 | Saadat et al. | |
| 2005/0251158 A1 | 11/2005 | Saadat et al. | |
| 2006/0047298 A1 | 3/2006 | Darzi et al. | |
| 2006/0106288 A1* | 5/2006 | Roth | A61B 17/0218 600/204 |
| 2006/0122462 A1 | 6/2006 | Roth et al. | |
| 2006/0200004 A1 | 9/2006 | Wilk | |
| 2006/0241344 A1 | 10/2006 | Wilk | |
| 2006/0241570 A1 | 10/2006 | Wilk | |
| 2007/0032702 A1 | 2/2007 | Ortiz | |
| 2007/0038239 A1 | 2/2007 | Ritchie | |
| 2007/0167960 A1 | 7/2007 | Roth et al. | |
| 2007/0276430 A1* | 11/2007 | Lee | A61B 1/00071 606/205 |
| 2008/0132933 A1 | 6/2008 | Gerber | |
| 2008/0172079 A1 | 7/2008 | Birk | |
| 2008/0249533 A1 | 10/2008 | Godin | |
| 2009/0093838 A1 | 4/2009 | Paganon | |
| 2009/0198266 A1 | 8/2009 | Cesare | |
| 2009/0287231 A1 | 11/2009 | Brooks et al. | |
| 2009/0299282 A1 | 12/2009 | Lau et al. | |
| 2010/0069882 A1* | 3/2010 | Jennings | A61M 25/0138 604/525 |
| 2010/0121371 A1 | 5/2010 | Brooks et al. | |
| 2010/0179417 A1 | 7/2010 | Russo | |
| 2011/0178454 A1 | 7/2011 | Gagner et al. | |
| 2011/0213390 A1 | 9/2011 | Kraemer et al. | |
| 2011/0288576 A1 | 11/2011 | Hoffman | |
| 2012/0022554 A1* | 1/2012 | Paik | A61B 17/29 606/130 |
| 2012/0065469 A1 | 3/2012 | Allyn et al. | |
| 2012/0165608 A1 | 6/2012 | Banik et al. | |
| 2012/0184981 A1 | 7/2012 | Pecor et al. | |
| 2012/0239061 A1 | 9/2012 | Mathur | |
| 2012/0277730 A1* | 11/2012 | Salahieh | A61B 1/00135 604/527 |
| 2013/0165774 A1 | 6/2013 | Nocca | |
| 2014/0018722 A1 | 1/2014 | Scott et al. | |
| 2014/0114121 A1 | 4/2014 | Trivedi | |

FOREIGN PATENT DOCUMENTS

| | | |
|---|---|---|
| EP | 2172156 A1 | 4/2010 |
| ES | 2326937 A1 | 10/2009 |
| JP | 3178309 U | 9/2012 |
| WO | 02096327 A2 | 12/2002 |
| WO | 2007110866 A2 | 10/2007 |
| WO | 2009/016834 A1 | 2/2009 |
| WO | 2009097585 A1 | 8/2009 |
| WO | 2011042893 A1 | 4/2011 |
| WO | 2011161148 A1 | 12/2011 |
| WO | 2012138737 A1 | 10/2012 |
| WO | 2013123235 A1 | 8/2013 |
| WO | 2014062881 A1 | 4/2014 |

OTHER PUBLICATIONS

European Search Report, dated Mar. 19, 2015, corresponding to European Application No. 14192226.0; 7 pages.
European Search Report, dated Mar. 24, 2015, corresponding to European Application No. 14192416.7; 7 pages.
Dietel et al., "Endoscopy of Vertical Banded Gastroplasty," The American Surgeon, May 1989, vol. 55; pp. 287-890.
Dietel et al., "Vertical Banded Gastroplasty: Results in 233 Patients," The Canadian Journal of Surgery, Sep. 1986, vol. 29, No. 5; pp. 322-324.
Mason et al., "Vertical Gastroplasty: Evolution of Vertical Banded Gastroplasty," World Journal of Surgery, Sep. 1998, vol. 22, No. 9; pp. 919-924.
Extended European Search Report dated Sep. 17, 2015, corresponding to European Patent Application 15167339.9; 10 pages.
European Search Report dated Dec. 2, 2015, corresponding to European Application No. 15177233.2; 7 pages.
European Communication, dated May 26, 2017, corresponding to European Application No. 15167342.3; 4 pages.
European Search Report, dated Mar. 24, 2017, corresponding to European Application No. 16199748.1; 5 pages.
European Search Report, dated Aug. 4, 2017, corresponding to European Application No. 14862145.1; 8 pages.

* cited by examiner

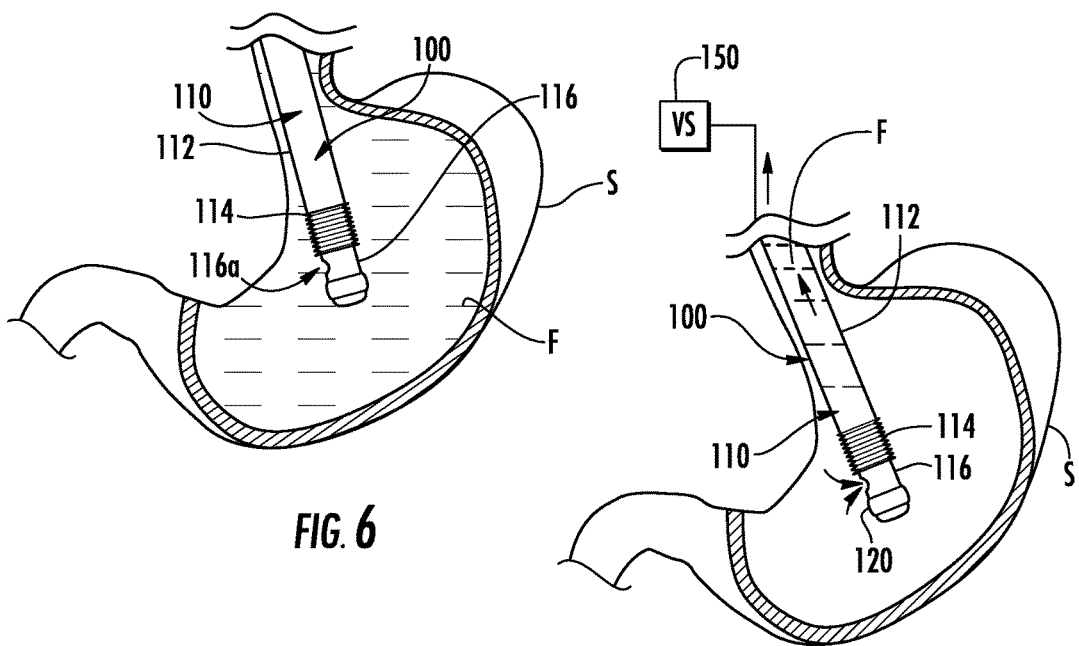
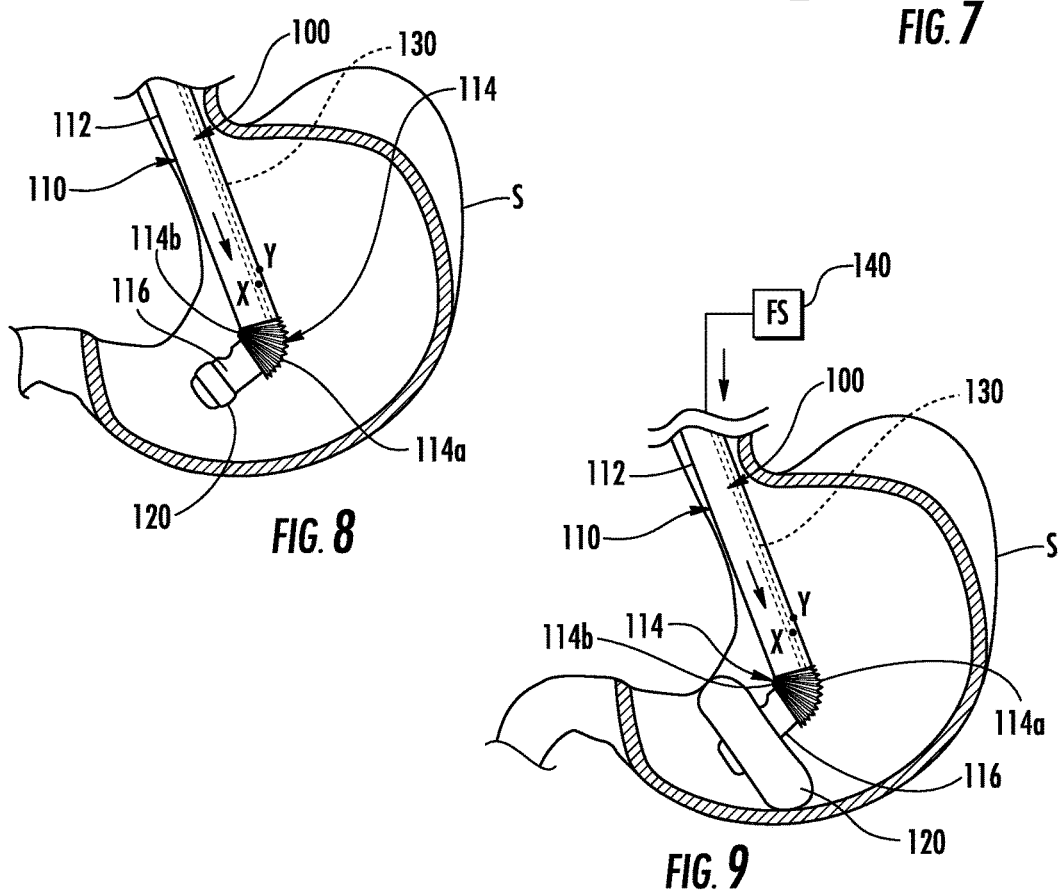

STEERABLE GASTRIC CALIBRATION TUBE

TECHNICAL FIELD

The present disclosure generally relates to surgical tools, and more particularly, to steerable gastric calibration tubes used in bariatric procedures.

BACKGROUND

A gastric calibration tube is a surgical tool used to effectuate a surgical procedure on a patient's stomach in an effort to reduce excessive obesity in the patient. In use, the tube is advanced into a patient's body through an oral cavity and down through the esophagus into the stomach to provide delineation of the antrum of the stomach, irrigation/suction of fluids, and/or a sizing of a gastric pouch. While being advanced, due at least in part to the circuitous nature of this track, a clinician may need to reposition the tube in various orientations until the tube is properly aligned or bypasses any obstruction(s). Increasing maneuverability of the tube can reduce the time to perform a desired procedure.

SUMMARY

According to one aspect of the present disclosure, a gastric calibration tube includes an elongate member and an adjusting member.

The elongate member has a length and includes a first segment and a second segment that extend along the length. The second segment includes a first side and a second side. The first and second sides are selectively movable in opposite lengthwise directions. The first and second sides are adapted to expand and collapse such that the first side collapses as the second side expands and the first side expands as the second side collapses. Movement of the first and second sides of the second segment in opposite lengthwise directions articulates a leading end portion of the elongate member relative to a trailing end portion of the elongate member. In certain embodiments, the second segment has a bellows configuration.

In some embodiments, the elongate member defines a side opening configured and dimensioned for at least one of aspiration and irrigation. The elongate member, in certain embodiments, includes a plurality of depth markings.

In some embodiments, the elongate member includes a third segment. The second segment is positioned between the first and third segments. The second and third segments are movable relative to the first segment.

The adjusting member is secured to one of the sides of the second segment and movable with the second segment relative to the first segment to steer the elongate member. The adjusting member is supported within the elongate member and an outer surface of the adjusting member is secured to an inner surface of the second segment of the elongate member. The adjusting member is movable between proximal and distal positions relative to the elongate member to move the first and second sides in opposite lengthwise directions.

In certain embodiments, the adjusting member is secured to one of the first and second sides of the second segment at multiple attachment points along the respective side of the second segment. In some embodiments, adjacent attachment points are positioned at spaced apart locations along the length of the elongate member. In some embodiments, the adjusting member is a coiled spring.

A balloon is supported on the elongate member and configured to receive inflation fluid to inflate the balloon.

According to another aspect, a gastric calibration tube includes an elongate member, an adjusting member, and a balloon supported on the elongate member configured to receive an inflation fluid to inflate the balloon.

The elongate member includes a leading end portion at a distal end of the elongate member and a trailing end portion at a proximal end of the elongate member. The elongate member defines a centerline that extends between leading and trailing end portions of the elongate member. The elongate member defines a side opening in an outer surface of the elongate member. The elongate member defines at least one lumen in fluid communication with the side opening. The at least one lumen is configured and dimensioned to couple to at least one of a fluid source and a vacuum source. In some embodiments, at least a portion of the leading end portion includes a bellows configuration. In some embodiments, the elongate member includes at least one depth marking.

The adjusting member is secured to a side surface of the leading end portion of the elongate member and is axially movable relative to the trailing end portion of the elongate member to move the side surface of the leading end portion and articulate the leading end portion of the elongate member relative to the trailing end portion of the elongate member. A movement of the adjusting member between proximal and distal positions moves diametrically opposed sides of the leading end portion of the elongate member in opposite lengthwise directions to articulate the leading end portion of the elongate member relative to the trailing end portion of the elongate member.

According to yet another aspect, a gastric calibration tube includes an elongate member including a leading segment, a trailing segment, and an intermediate segment positioned between the leading and trailing segments. An inflatable balloon is secured to the leading segment. The intermediate segment is adjustable to move the intermediate segment and the leading segment relative to the trailing segment. A movement of the intermediate segment articulates the leading segment relative to the trailing segment.

Other aspects, features, and advantages will be apparent from the description, the drawings, and the claims.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 6 is a side view of the gastric calibration tube shown in an unarticulated position within a stomach;

FIG. 7 is a side view of the gastric calibration tube aspirating fluid out of the stomach;

FIG. 8 is a side view of the gastric calibration tube shown in an articulated position within the stomach; and FIG. 9 is a side view of the gastric calibration tube shown in the articulated position with a balloon of the gastric calibration tube shown in an inflated state within the stomach.

DETAILED DESCRIPTION

As used herein, the term "clinician" refers to a doctor, nurse, or other care provider and may include support personnel. The terms "proximal" or "trailing" each refer to the portion of a structure closer to a clinician, and the terms "distal" or "leading" each refer to a portion of a structure farther from the clinician.

Figures 1A, 1B:
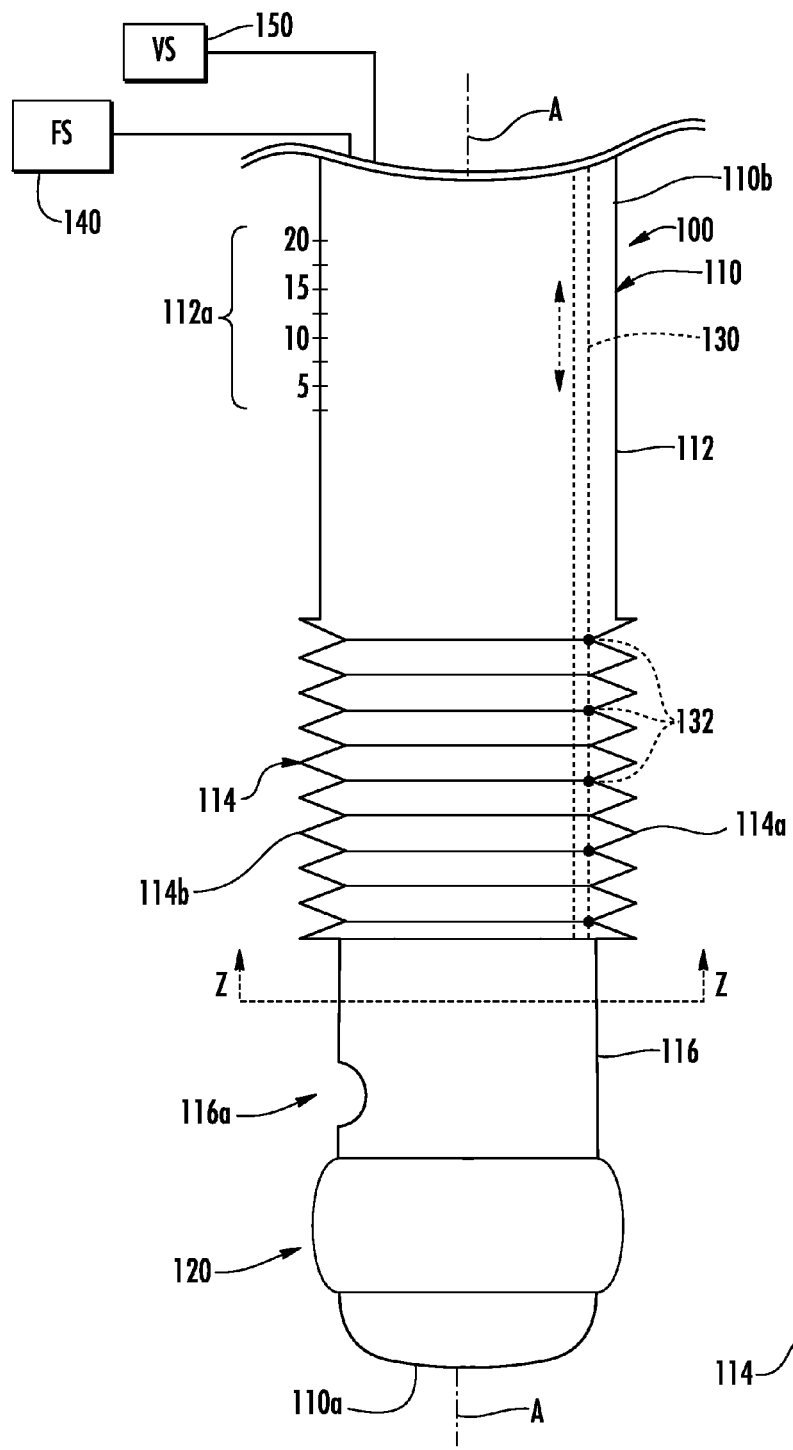
FIG. 1A is a side view of a leading end portion of an embodiment of a gastric calibration tube shown coupled to a fluid source and a vacuum source in accordance with the principles of the present disclosure.
FIG. 1B is cross-sectional view of the gastric calibration tube taken along line Z-Z.
Figure 2:
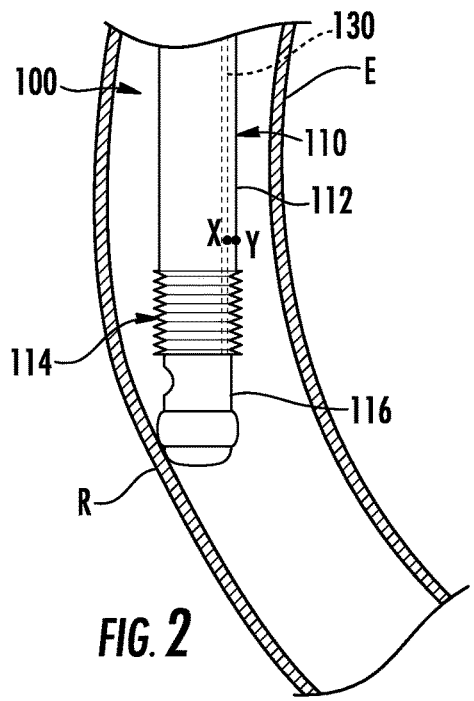
FIGS. 2-5 are progressive, side views of the gastric calibration tube navigating through an esophagus.
Figure 3:
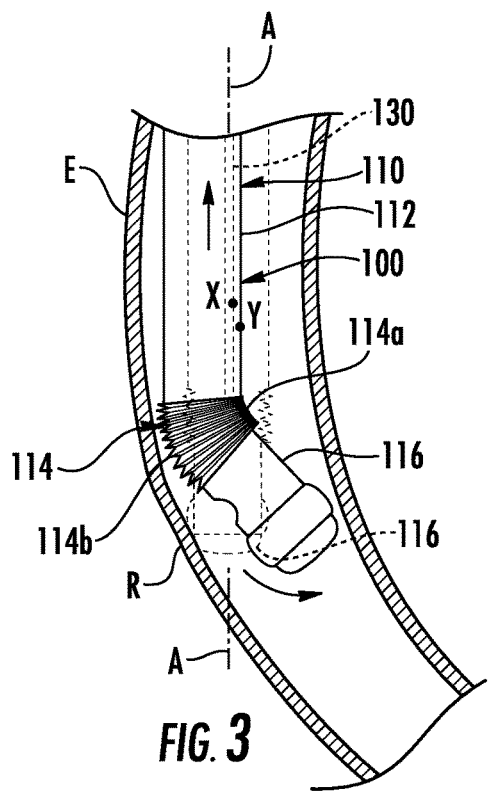
Figure 4:
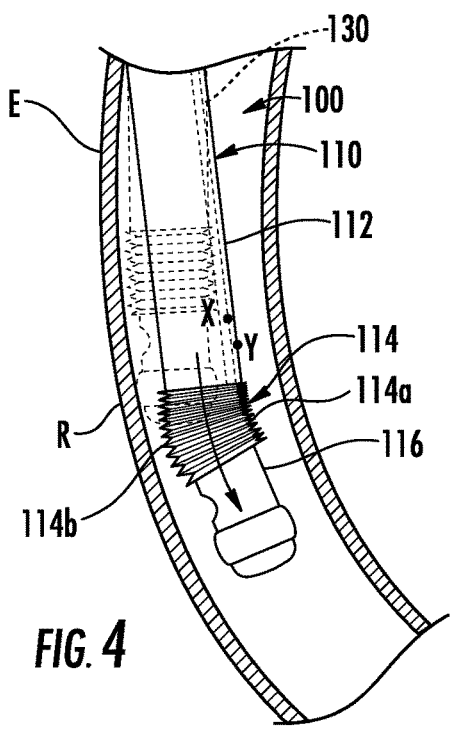
Figure 5:
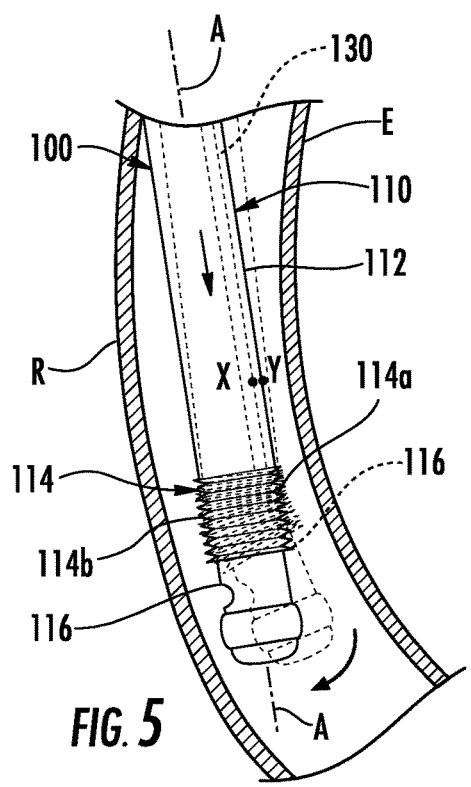

Referring now to FIG. 1A, a gastric calibration tube 100 includes an elongate member 110, an inflatable balloon 120 supported on the elongate member 110, and an adjusting line or member 130 secured to a portion of the elongate member 110 and movable relative to another portion of the elongate member 110 to steer the elongate member 110. It should be appreciated that, as used herein, the term balloon refers to any structure defining a volume that is expandable upon introduction of fluid into the volume and, thus, can include a unitary arrangement of material and/or a multi-component arrangement secured together to form, for example, a bladder.

In use, as described in further detail below with reference to FIGS. 2-9, the gastric calibration tube 100 is inserted into an oral cavity of a patient and is advanced distally (e.g., caudally) along a track that extends between the oral cavity and the stomach of the patient. If the gastric calibration tube 100 encounters an obstruction or otherwise becomes misaligned during advancement along the track, a leading end portion of the elongate member 110 can be articulated to maneuver the gastric calibration tube 100 away from the obstruction or back into alignment by applying a pushing and/or pulling force to the adjusting member 130. When the gastric calibration tube 100 is positioned in the stomach (e.g., the antrum or lower portion of the stomach), the balloon 120 can be inflated to fix the gastric calibration tube 100 within the stomach and aid a clinician in performing a bariatric surgical procedure such as sleeve gastrectomy. For example, in a sleeve gastrectomy procedure, with the balloon 120 inflated in the antrum of the stomach, a clinician can remove a portion of the stomach and staple the remaining portion together to limit the size of the patient's stomach for helping the patient lose weight.

Referring again to FIG. 1A, the elongate member 110 can be formed of any material with sufficient flexibility to enable the gastric calibration tube 100 to maneuver along the patient's track between the oral cavity and the stomach. The elongate member 110 has a leading end portion 110a and a trailing end portion 110b and defines a centerline "A" that extends between the leading and trailing end portions 110a, 110b.

The elongate member 110 includes a trailing segment 112, an intermediate segment 114, and a leading segment 116. The intermediate segment 114 is positioned between the trailing and leading segments 112, 116 and is articulable with the leading segment 116 relative to the trailing segment 112 between an unarticulated position and an articulated position. In some embodiments, the trailing segment 112 includes one or more depth markings 112a that function to identify an insertion depth of the gastric calibration tube 100 relative to the track. A leading end portion of the trailing segment 112 is secured to a trailing end portion of the intermediate segment 114 and a leading end portion of the intermediate segment 114 is secured to a trailing end portion of the leading segment 116. In certain embodiments, the intermediate segment 114 has a bellows configuration. The leading segment 116 extends to the leading end portion 110a of the elongate member 110 and defines a side opening 116a. The side opening 116a can have any geometric shape including polygonal configurations, circular configurations, and/or combinations thereof. The balloon 120 is secured to an outer surface of the leading segment 116 at a position adjacent to the side opening 116a.

Referring also to FIG. 1B, the elongate member 110 defines a first lumen 116b that is in fluid communication with the side opening 116a of the elongate member 110 and a second lumen 120a that is in fluid communication with the balloon 120. While two lumens are shown, additional lumens are possible. A fluid source 140 and/or a vacuum source 150 can be coupled to the first and/or second lumens 116b, 120a to enable proximal and/or distal fluid movement through the first and/or second lumens 116b, 120a. For example, when the fluid source 140 is coupled to the first lumen 116b, fluid (e.g., saline) can be passed from the fluid source 140, through the first lumen 116, and out of the side opening 116a to irrigate a surgical site such as the stomach. When the fluid source 140 is coupled to the second lumen 120a, the fluid can be passed from the fluid source 140 to the balloon 120 to inflate the balloon 120. Similarly, when the vacuum source 150 is operably coupled to the first lumen 116b, bodily fluid can be drawn, by virtue of a vacuum created in the respective lumen by the vacuum source 150, into the side opening 116a to aspirate the bodily fluid through the first lumen 116a. Alternately, and/or additionally, when the vacuum source 150 is coupled to the second lumen 120a, the vacuum source 150 creates a vacuum in the second lumen 120a that draws the fluid out of the balloon 120 and through the second lumen 120a to partially and/or wholly deflate the balloon 120.

The adjusting member 130 is positioned within the elongate member 110. In some embodiments, the adjusting member 130 is positioned within a channel formed between inner and outer walls of the elongate member 110. In certain embodiments, the channel is an annulus. An outer surface of the adjusting member 130 is secured to an inner surface of the intermediate segment 114 on a first side 114a of the intermediate segment 114. The adjusting member 130 and the intermediate segment can be secured together at one or more attachment points 132 along the intermediate segment 114. The attachment points 132 enable the first side 114a of the intermediate segment 114 to move relative to the trailing segment 112 (and centerline "A") between proximal and distal positions with the adjusting member 130 as the adjusting member 130 moves within the elongate member 130 relative to the trailing segment 112 between proximal and distal positions (e.g., lengthwise and/or generally parallel relative to the centerline "A"). For example, as illustrated in FIGS. 2-5, a point "X" on the adjusting member 130 moves proximally and/or distally relative to a point "Y" on the trailing segment 112 of the elongate member 110 as the adjusting member 130 moves proximally and/or distally relative to the trailing segment 112 to articulate the leading end portion 110a to an articulated position (see FIG. 3). Notably, when the point "X" is aligned with the point "Y," the gastric calibration tube 100 is in an unarticulated position (see FIG. 2).

It should be understood that the adjusting member 130 can be secured, for example, at a trailing end of the adjusting member 130, to any suitable actuating member (e.g., a knob, button, slide, etc.) (not shown) adapted to impart a pushing and/or pulling force to the adjusting member 130 upon rotational and/or lengthwise movement of the actuating member.

In an exemplary use, as illustrated in FIGS. 2-5, the gastric calibration tube 100 is inserted into a patient and is advanced distally toward the stomach down a track that extends along the esophagus "E." Upon encountering an obstruction or becoming misaligned, for example, when the leading end 110a of the gastric calibration tube 100 is frictionally restricted by curvature in the esophagus "E" at a point of restriction "R" that inhibits the gastric calibration tube 100 from advancing distally along the esophagus "E," a pushing and/or pulling force can be applied to the adjusting member 130 to proximally and/or distally move the adjusting member 130 relative to the trailing segment 112 of the elongate member 130 (e.g., generally axially relative to the centerline "A").

Because the first side 114a of the intermediate segment 114 is secured to the adjusting member 130 at attachment points 132, the first side 114a of the intermediate segment 114 is adapted to move with the adjusting member 130 between proximal and distal positions. More particularly, proximal movement of the adjusting member 130 collapses and outwardly curves the first side 114a of the intermediate segment 114 relative to the centerline "A" (see FIG. 3) and distal movement of the adjusting member 130 expands and inwardly curves the first side 114a of the intermediate segment 114 relative to the centerline "A" (see FIG. 5).

A second side 114b of the intermediate segment 114, which is positioned in diametrical opposition to the first side 114a, is adapted to move in the opposite lengthwise direction of the lengthwise movement of the first side 114a of the intermediate segment 114 as the adjusting member 130 moves with the first side 114a of the intermediate segment 114. It should be understood that as the first and second sides 114a, 114b move in generally opposite lengthwise directions relative to the centerline "A," the leading segment 116 and the intermediate segment 114 articulate relative to the trailing segment 112. Specifically, as the first side 114a collapses and curves (or straightens) in one or more direction(s), the second side 114b expands and curves (or straightens) in opposite directions, articulating the intermediate segment 114 and the leading segment 116 to toward to first side 114a (e.g., toward the right). Similarly, as the first side 114a expands, the second side 114b collapses, articulating the intermediate segment 114 and the leading segment 116 toward the second side 114b (e.g., toward the left).

As can be appreciated, the gastric calibration tube 100 is articulable, as described above, as necessary to enable the gastric calibration tube 100 to be navigated along the track.

Referring also to FIGS. 6-7, when the gastric calibration tube 100 is positioned in the stomach "S," the vacuum source 150 functions to aspirate bodily fluid "F" in the stomach "S" through the side opening 116a.

With reference to FIG. 8, the gastric calibration tube 100 can be articulated, as described above, within the stomach "S" to position the balloon 120 at any suitable location within the stomach "S" such as the antrum or lower portion of the stomach "S."

As shown in FIG. 9, the fluid source 140 functions to partially and/or wholly inflate the balloon 120 to fix the gastric calibration tube 100 within the stomach "S" and aid the clinician in performing a bariatric surgical procedure as described above.

Although shown as an elongate strip, in some embodiments, the adjusting member 130 has a coiled spring configuration. In certain embodiments, the adjusting member 130 includes a plurality of adjusting members 130. As it can be appreciated, each adjusting member 130 can be secured to any suitable location on the elongate member sufficient to enable articulation of the intermediate and leading segments 114, 116 of the elongate member 110. For example, any number of adjusting members 130 can be positioned at predetermined locations (e.g., spaced apart) on the inner and/or outer surfaces of the elongate member 110. Additional adjusting members provide added flexibility and adjustability to manipulate the intermediate segment 114 and steer the leading segment 116 relative to the trailing segment 112.

Any of the components of the presently disclosed gastric calibration tube can be formed of any suitable metallic and/or polymeric material. Securement of any of the components of the presently disclosed gastric calibration tube can be effectuated using known fastening techniques such welding, crimping, gluing, etc.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A gastric calibration tube for performing a bariatric procedure within a patient's stomach, the gastric calibration tube comprising:
   an elongate member having a length and including a first segment and a second segment that extend along the length of the elongate member, the second segment having a bellows configuration including an outer surface that extends to outer apices and an inner surface that extends to inner apices, the second segment including a first side and a second side, the first and second sides being selectively movable in opposite lengthwise directions; and
   an adjusting line fixedly secured to at least some of the inner apices of the bellows configuration with each inner apex of the at least some inner apices being a separate attachment point on one of the first or second sides of the second segment, the adjusting line positioned to pull the bellows configuration at the separate attachment points to move the second segment relative to the first segment in order to steer the gastric calibration tube within the patient's stomach.

2. The gastric calibration tube of claim 1, wherein adjacent attachment points are positioned at spaced apart locations along the length of the elongate member.

3. The gastric calibration tube of claim 1, wherein the elongate member defines a side opening configured and dimensioned for at least one of aspiration and irrigation.

4. The gastric calibration tube of claim 1, wherein the elongate member further includes a third segment, the second segment being positioned between the first and third segments, the second and third segments being movable relative to the first segment.

5. The gastric calibration tube of claim 1, wherein the elongate member includes a plurality of depth markings.

6. The gastric calibration tube of claim 1, wherein a balloon is supported on the elongate member and configured to receive inflation fluid to inflate the balloon.

7. The gastric calibration tube of claim 1, wherein the adjusting line is a coiled spring.

8. The gastric calibration tube of claim 1, wherein the adjusting line is movable between proximal and distal positions relative to the elongate member to move the first and second sides in opposite lengthwise directions.

9. The gastric calibration tube of claim 1, wherein the adjusting line is supported within the elongate member and an outer surface of the adjusting line is secured to an inner surface of the second segment of the elongate member.

10. The gastric calibration tube of claim 1, wherein the first and second sides are adapted to expand and collapse such that the first side collapses as the second side expands and the first side expands as the second side collapses.

11. The gastric calibration tube of claim 1, wherein the elongate member includes leading and trailing end portions, wherein movement of the first and second sides of the second segment in opposite lengthwise directions articulates the leading end portion of the elongate member relative to the trailing end portion.

12. A gastric calibration tube for performing a bariatric procedure within a patient's stomach, the gastric calibration tube comprising:
a unitary elongate member including a leading end portion at a distal end of the elongate member and a trailing end portion at a proximal end of the elongate member, the elongate member defining a centerline that extends between the leading and trailing end portions, wherein at least a portion of the leading end portion includes a bellows configuration, the bellows configuration including an outer surface that extends to outer apices and an inner surface that extends to inner apices;
an adjusting line fixedly secured to at least some of the inner apices of the bellows configuration with each inner apex of the at least some inner apices being a separate and distinct attachment point on a side surface of the leading end portion of the elongate member, the adjusting line positioned to pull the bellows configuration at the separate and distinct attachment points to articulate the leading end portion of the elongate member relative to the trailing end portion of the elongate member in order to steer the gastric calibration tube within the patient's stomach; and
a balloon supported on the elongate member, the balloon configured to receive an inflation fluid to inflate the balloon.

13. The gastric calibration tube of claim 12, wherein the elongate member defines a side opening in an outer surface of the elongate member, the elongate member defining at least one lumen in fluid communication with the side opening, the at least one lumen coupled to at least one of a fluid source and a vacuum source.

14. The gastric calibration tube of claim 12, wherein the elongate member includes at least one depth marking.

15. The gastric calibration tube of claim 12, wherein the adjusting line is a coiled spring.

16. The gastric calibration tube of claim 12, wherein movement of the adjusting line between proximal and distal positions moves diametrically opposed sides of the leading end portion of the elongate member in opposite lengthwise directions to articulate the leading end portion of the elongate member relative to the trailing end portion of the elongate member.

17. A gastric calibration tube for performing a bariatric procedure within a patient's stomach, the gastric calibration tube comprising:
an adjusting line;
a unitary elongate member including a leading segment, a trailing segment, and an intermediate segment having a bellows configuration positioned between the leading and trailing segments, the bellows configuration including an outer surface that extends to outer apices and an inner surface that extends to inner apices, at least some of the inner apices fixedly attached to the adjusting line to enable the bellows configuration to be pulled by the adjusting line, the intermediate segment adjustable to move the intermediate segment and the leading segment relative to the trailing segment, wherein a movement of the intermediate segment articulates the leading segment relative to the trailing segment in order to steer the gastric calibration tube within the patient's stomach; and
an inflatable balloon secured to the leading segment.

18. The gastric calibration tube of claim 1, wherein the gastric calibration tube includes a blunt round tip coupled to a distal end of the second segment.

* * * * *